United States Patent [19]

Mizobuchi et al.

[11] Patent Number: 4,876,092
[45] Date of Patent: Oct. 24, 1989

[54] SHEET-SHAPED ADHESIVE PREPARATION APPLICABLE TO ORAL CAVITY

[75] Inventors: Tadafumi Mizobuchi; Akihito Ohji, both of Kagawa; Seiichi Sakoh, Anan; Yasuyoshi Muguruma, Kagawa, all of Japan

[73] Assignee: Teikoku Seiyaku Kabushiki Kaisha, Kagawa, Japan

[21] Appl. No.: 8,771

[22] Filed: Jan. 30, 1987

[30] Foreign Application Priority Data

Feb. 1, 1986 [JP] Japan .................................. 61-020468

[51] Int. Cl.$^4$ ....................... A61K 13/00; B32B 23/04
[52] U.S. Cl. ..................... 424/435; 424/448; 424/434; 514/953; 428/323; 428/532; 428/216
[58] Field of Search ............... 428/532, 216; 427/395; 514/900, 901, 902, 946, 947, 953; 424/435, 448, 434

[56] References Cited

U.S. PATENT DOCUMENTS

| 2,980,554 | 4/1961 | Gentile et al. | 428/532 |
| 4,123,592 | 10/1978 | Rainer et al. | 428/532 |
| 4,406,708 | 9/1983 | Hesselgren | 428/532 X |
| 4,432,975 | 2/1984 | Libby | 514/946 |
| 4,569,837 | 2/1986 | Suzuki et al. | 514/953 |

Primary Examiner—P. C. Ives
Attorney, Agent, or Firm—Birch, Stewart, Kolasch & Birch

[57] ABSTRACT

A sheet-shaped adhesive preparation comprising an adhesive layer containing as essential components a carboxyvinyl polymer, a water-insoluble methacrylic copolymer, a polyhydric alcohol and a pharmaceutically active agent, and a water-impermeable and water-insoluble carrier layer containing as essential components a pharmaceutically acceptable water-insoluble, film-forming high molecular weight compound and a plasticizer, which can adhere within the oral cavity for a longer period of time and can release the active agent and hence is useful as a sustained release preparation for the oral cavity.

16 Claims, 6 Drawing Sheets

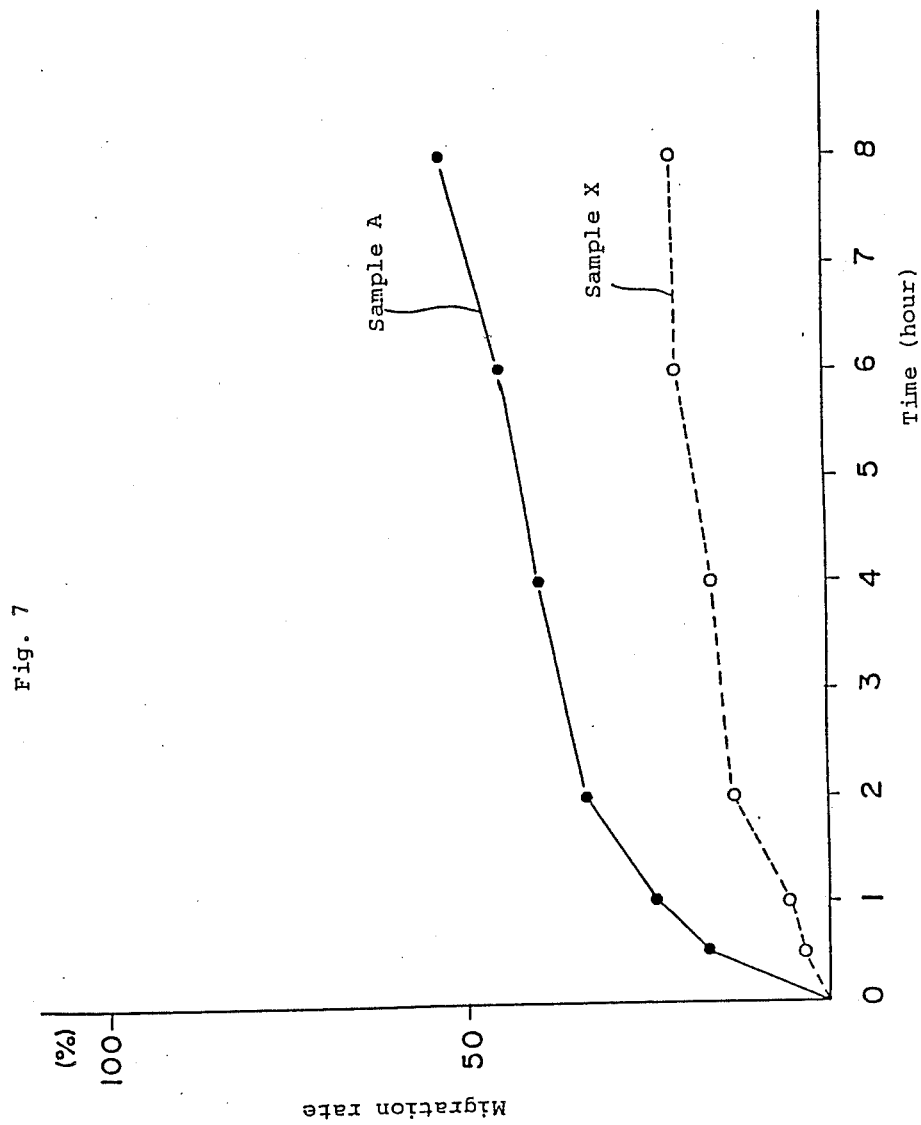

SHEET-SHAPED ADHESIVE PREPARATION APPLICABLE TO ORAL CAVITY

The present invention relates to a sheet-shaped adhesive preparation which is applied to the oral cavity. More particularly, the present invention relates to a sheet-shaped adhesive preparation comprising an adhesive layer containing as essential components a carboxyvinyl polymer, a water-insoluble methacrylic copolymer, a polyhydric alcohol and a pharmaceutically active agent, and a water-impermeable and water-insoluble carrier layer containing as essential components a pharmaceutically acceptable water-insoluble, film-forming high molecular weight compound and a plasticizer, which is applicable to the mucous membrame within the oral cavity.

Prior Art

There have hitherto been known various sustained release preparations applicable to the oral cavity, such as sublingual tablets, trouches, buccals, etc., but these preparations are hard and thick and hence persons using them are aware of the device and often chew and swallow the preparations within a short period of time. Accordingly, these known preparations are not necessarily satisfactory as a preparation for use in the oral cavity. Additionally, there has recently been marketed a tablet for stomatitis which is applicable directly to the affected region, but this preparation is also hard and has a certain thickness and hence persons using it are aware of its presence. Accordingly, the tablet may be dislodged with the tongue and swallowed during eating and drinking, and hence it is difficult to retain within the oral cavity for a long time. Moreover, the know preparations are usually coposed of components which are soluble or disintegrable within the mouth, and hence, the pharmaceutically active agents contained in the preparations are mostly swallowed without being absorbed through the mucous membrane in the oral cavity. Thus, these preparations are not necessarily satisfactory as a sustained release preparation for the oral cavity.

BRIEF SUMMARY OF THE INVENTION

The present inventors have intensively studied an improved sustained release preparation applicable to the oral cavity which can be adhered on the mucous membrane in the oral cavity for a long period of time and can gradually release a pharmaceutically active agent through the mucous membrane in the oral cavity, and have found that the desired preparation suitable for topically and/or administering a medicament can be obtained by forming a sheet-shaped adhesive preparation comprising a specific adhesive layer composed of specific components and a specific water-impermeable and water-insoluble carrier layer and that when the preparation is applied to the mucous membrane in the oral cavity, it is easily adhered thereto and can be maintained for a long period of time without being affected by secreted fluid (e.g. saliva) or without being swallowed even during eating, drinking or speaking, and thereby the pharmaceutically active agent can gradually and effectively be released.

An object of the invention is to provide a sheetshaped adhesive preparation applicable to the oral cavity which can gradually and effectively release the pharmaceutically active agent. Another object of the invention is to provide a sheet-shaped adhesive preparation comprising a specific adhesive layer and a specific water-impermeable and water-insoluble carrier layer. A further object of the invention is to provide a sheet-shaped adhesive preparation which can be applied to the mucous membrane in the oral cavity and can be maintained in position for a long period of time without being peeled off and swallowed even during eating, drinking and speaking. These and other objects and advantages of the invention will be apparent to skilled persons from the following description.

BRIEF DESCRIPTION OF THE DRAWING

The present invention will become more fully understood from the detailed description given hereinbelow and the accompanying drawings which are given by way of illustration only, and thus are not limitative of the present invention, and wherein:

FIG. 7 is a graph showing the correlation between the migration rate and time which is obtained by the migration test of Sample A and Sample N.

Figure 1:
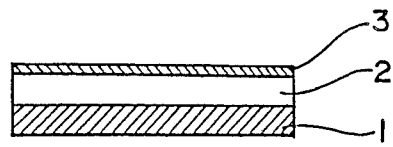
FIG. 1 and FIG. 2 each show a sectional view of the sheet-shaped adhesive preparation applicable to the oral cavity of the present invention.

In the figures, element
1 is a carrier layer, element 2 is an adhesive layer, element 3 is a release paper, element i is a rotating shaft, element ii and IV are test solutions, element iii is a rotor blade, elements iv, a and III are samples, element b is plate, element c is a 5% polyacrylamide solution, element I is a rubber stopper, and element II is a dialysis membrane.

DETAILED DESCRIPTION OF THE INVENTION

The sheet-shaped adhesive preparation of this invention comprises an adhesive layer containing as essential components a carboxyvinyl polymer, a water-insoluble methacrylic copolymer, a polyhydric alcohol and a pharmaceutically active agent, and a water-impermeable and water-insoluble carrier layer containing as essential components a pharmaceutically acceptable water-insoluble, film-forming high molecular weight compound and a plasticizer.

The water-insoluble methacrylic copolymer used for the adhesive layer includes all copolymers which are usually used as a coating agent for tablets etc., for example, ethyl acrylate-methyl methacrylate-trimethylammonium-ethyl methacrylate chloride copolymer, dimethylaminoethyl methacrylate-methyl methacrylate copolymer, and the like, which may be used alone or in combination of two or more thereof.

The carboxyvinyl polymer includes polyacrylic acid, a partly crosslinked product thereof, for example, an acid type product such as Carbopol which is a commercially available product.

The polyhydric alcohol includes, for example, glycerin, propylene glycol, polyethylene glycol, 1,3-butanediol, sorbitol, and the like, which may be used alone or in combination of two or more thereof.

The water-insoluble, film-forming high molecular weight compound used for the carrier layer in this invention includes, for example, water-insoluble cellulose derivatives, such as ethyl cellulose having 1.5 or more of degree of substitution of ethoxy group, cellulose acetate phthalate, hydroxypropyl methyl cellulose phthalate, and the like, which may be used alone or in combination of two or more thereof.

The plasticizer includes, for example, castor oil, triacetin, the same polyhydric alcohols as mentioned above, which may be used alone or in combination of two or more thereof.

The pharmaceutically active agent includes all medicaments which can be absorbed from the mucous membrane in the oral cavity, for example, benzodiazepin analogs, psychotropic agents, antispasmodics, antihistamines, steroidal and non-steroidal antiinflammatory agents, cardiotonics, antiarrhythmic agents, diuretics, antihypertensives, vascoconstrictors, vasodilators, nitrate agents, calcium antagonists, antiallergic agents, agents for oral diseases, agents for dental diseases, hormones, vitamins, agents for quitting smoking, antitumor agents, antibioties, and chemotherapeutics, and the like. Among these, preferred agents are agents which show high physiological activities in a comparatively small dose, agents which are easily metabolized when administered orally, agents which injure digestive organs, agents which are hardly utilized, agents which are used in the form of an injection (e.g. subcutaneous injection), and the like.

The carboxyvinyl polymer and the water-insoluble methacrylic copolymer contained in the adhesive layer are used in a ratio of 5:1 to 200:1 by weight, preferably 50:1 to 150:1 by weight (carboxyvinyl polymer:methacrylic copolymer), and the amount of both is in the range of 40 to 98 w/w %, preferably 60 to 95 w/w %, based on the total weight of all components in the adhesive layer. The other component, polyhydric alcohol is incorporated in an amount of 1 to 50 w/w %, preferably 5 to 20 w/w %, based on the total weight of all components in the adhesive layer. The amount of the pharmaceutically active agent depends on the kinds of the agents and the desired effect thereof, but is usually in the range of 0.1 to 50 w/w %, preferably 1 to 30 w/w %, based on the total weight of the adhesive layer.

The water-insoluble, film-forming high molecular weight compound and the plasticizer in the water-impermeable and water-insoluble carrier layer are incorporated in a ratio of 20:1 to 1:1 by weight, preferably 10:1 to 3:2 by weight, (high molecular weight compound:plasticizer).

The adhesive layer has a thickness of 10 to 480 μm, preferably 20 to 300 μm, and the carrier layer has a thickness of 10 to 200 μm, preferably 20 to 150 μm. The sheetshaped adhesive preparation comprising the adhesive layer and carrier layer has a total thickness of 20 to 500 82 m, preferably 50 to 350 μm. The sheet-shaped adhesive preparation for the oral cavity does not give any unusual sensation to the persons when applied, and is flexible and shows excellent initial adhesion and can be adhered onto the mucous membrane of the oral cavity and thereby can gradually and effectively release the pharmaceutically active agent.

When a water-permeable or water-soluble or -disintegrable carrier layer is used instead of the waterimpermeable and water-insoluble carrier layer, the adhesive layer releases the active ingredients too quickly and hence the pharmaceutically active agent is mostly swallowed. Furthermore, if no carrier layer is present, the pharmaceutically active agent is mostly swallowed and further the sheet-shaped adhesive preparation can not be adhered onto the mucous membrane in the oral cavity for a long period of time. When the carboxyvinyl polymer is incorporated in a larger ratio than the above-mentioned range of the carboxyvinyl polymer and the water-insoluble methacrylic copolymer in the adhesive layer, the sheet-shaped adhesive preparation can not be adhered for a long period of time, and on the other hand, when the carboxyvinyl polymer is incorporated in lesser ratio, the preparation shows inferior initial adhesion and also show inferior release of the active agent. If the sheet-shaped adhesive preparation of this invention has too great a thickness, persons using it have a strange and bad sensation and hence peel it off with the tongue, thereby the preparation can not be adhered for a long period of time, and on the other hand, if the preparation is too thin, the pharmaceutically active agent can not be incorporated into the preparation in an amount sufficient for exhibiting the desired activity.

The sheet-shaped adhesive preparation applicable to the oral cavity of the present invention may also contain other conventional additives, such as excipients (e.g. titanium oxide, talc, etc.), colorants (e.g. pigments, etc.), and the like.

The preparation for the oral cavity of this invention can be prepared in the following manner.

The components for the adhesive layer are uniformly mixed in an appropriate solvent (e.g. ethyl alcohol, etc.), and the mixture is spread onto a release paper in a desired thickness in a conventional manner, and then it is dried to give a sheet-like adhesive layer. Separately, the components for the carrier layer are dissolved in an appropriate solvent likewise, and the mixture is spread and laminated onto the sheet-like adhesive layer as prepared above, and then dried. The laminated sheet thus obtained is cut in a desired size to give the desired sheet-shaped adhesive preparation profile applicable to the oral cavity as shown in the accompanying FIG. 1.

Figure 2:
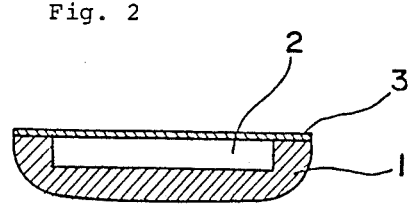

Alternatively, the sheet-like adhesive layer as prepared above is cut in a desired size, and thereon a solution of the components for the carrier layer is sprayed or coated so that the carrier layer covers and surrounds the adhesive layer, and dried to give the desired sheet-shaped adhesive preparation profile as shown in FIG. 2.

This invention is illustrated by the following Examples but should not be construed to be limited thereto. Desirable properties of the sheet-shaped adhesive preparation of this invention is demonstrated by Experiments.

EXAMPLE 1

Composition for adhesive layer:

| Ingredients | Amount |
| --- | --- |
| Hiviswako (carboxyvinyl polymer) | 12 g |
| Eudragit RS (ethyl acrylate-methyl methacrylate-trimethylammonium-ethyl methacrylate chloride copolymer) | 0.12 g |
| Polyethylene glycol 400 | 2 g |
| Titanium oxide | 0.6 g |
| Triamcinolone acetonide | 0.06 g |
| Ethanol | 140 ml |

The above ingredients are mixed and dissolved by kneading to give a uniform paste.

Composition for carrier layer:

| Ingredients | Amount |
| --- | --- |
| Ethocel (STD) (ethyl cellulose having ethoxy content of 48-49.5) | 15 g |
| Castor oil | 4 g |
| Red No. 2 pigment | 10 mg |
| Ethanol | 140 ml |

The above ingredients are mixed well to give a uniform paste.

The composition for adhesive layer prepared above is spread onto a release paper and dried to give a sheetlike adhesive layer (thickness of the adhesive layer: 100 μm). Subsequently, the composition for carrier layer is spread onto the sheet-like adhesive layer and then dried to form a carrier layer (thickness of the carrier layer: 50 μm). The sheet thus obtained is cut in a fixed size (0.5cm$^2$) to give a sheet-shaped adhesive preparation profile for the oral cavity as shown in FIG. 1, wherein triamcinolone acetonide is contained in an amount of 25 μg per one sheet).

EXAMPLE 2

A sheet-like adhesive layer as prepared in the same manner as described in Example 1 is cut in a fixed size (0.5 cm$^2$), and on the piece of adhesive layer is spread a composition for carrier layer as prepared in the same manner as described in Example 1 in a fixed thickness, and the resultant is dried to give a sheet-shaped adhesive preparation profile for the oral cavity (thickness of adhesive layer: 100 μm, thickness of carrier layer: 50 μm) as shown in FIG. 2, wherein triamcinolone acetonide is contained in an amount of 25 μg per one sheet.

EXAMPLE 3

Composition for adhesive layer:

| Ingredients | Amount |
| --- | --- |
| Hiviswako | 12 g |
| Eudragit RS | 0.2 g |
| Propylene glycol | 2.08 g |
| Titanium oxide | 0.6 g |
| Dexamethasone | 0.06 g |
| Ethanol | 140 ml |

Composition for carrier layer:

| Ingredients | Amount |
| --- | --- |
| Cellulose acetate phthalate | 12 g |
| Triacetin | 7 g |
| Red No. 2 pigment | 10 mg |
| Acetone | 140 ml |

In the same manner as described in Example 1, by using the above formulation, there are prepared the composition for adhesive layer and the composition for carrier layer, respectively, and by using these compositions, there is prepared a sheet having an adhesive layer (thickness: 100 μm) and a carrier layer (thickness: 100 μm). The sheet is cut in a size of 0.5 cm$^2$ to give a sheet-shaped adhesive preparation for the oral cavity as shown in FIG. 1, wherein dexamethasone is contained in an amount of 25 μg per one sheet.

EXAMPLE 4

In the same manner as described in Example 2 by using the same formulation as used in Example 3, there is prepared a sheet-like adhesive layer, and it is cut in a size of 0.5 cm$^2$, and thereon is spread and formed a carrier layer, followed by drying to give a sheet-shaped adhesive preparation for the oral cavity (thickness of adhesive layer: 100 μm, thickness of carrier layer: 50 μm) as shown in FIG. 2, wherein dexamethasone is contained in an amount of 25 μg per one sheet.

EXAMPLE 5

Composition for adhesive layer:

| Ingredients | Amount |
| --- | --- |
| Hiviswako | 12 g |
| Eudragit E (dimethylaminoethyl methacrylate-methyl methacrylate copolymer] | 0.25 g |
| Polyethylene glycol 400 | 2 g |
| Indomethacin | 8.13 g |
| Ethanol | 105.62 g |

Composition for carrier layer:

| Ingredients | Amount |
| --- | --- |
| Hydroxypropyl cellulose phthalate | 17 g |
| Glycerin | 3 g |
| Ethanol | 70 ml |
| Acetone | 70 ml |

In the same manner as described in Example 1, by using the above formulation, there are prepared the composition for adhesive layer and the composition for carrier layer, respectively, and by using these compositions, there is prepared a sheet having an adhesive layer (thickness: 150 82 m) and a carrier layer (thickness: 25 μm). The sheet is cut in a size of 1 cm$^2$ to give a sheet-shaped adhesive preparation for the oral cavity as shown in FIG. 1, wherein indomethacin is contained in an amount of 5 mg per one sheet.

EXAMPLE 6

Composition for adhesive layer:

| Ingredients | Amount |
| --- | --- |
| Hiviswako | 12 g |
| Eudragit RS | 0.2 g |
| 1,3-Butanediol | 4 g |
| Titanium oxide | 0.6 g |
| Nicotine | 6.13 g |
| Ethanol | 135 ml |

Composition for carrier layer:

| Ingredients | Amount |
| --- | --- |
| Ethocel (STD) | 15 g |
| Glycerin | 5 g |
| Red No. 2 pigment | 10 mg |
| Ethanol | 140 ml |

In the same manner as described in Example 1, by using the above formulation, there are prepared the composition for adhesive layer and the composition for carrier layer, respectively, and by using these compositions, there is prepared a sheet having an adhesive layer (thickness: 150 μm) and a carrier layer (thickness: 50 μm). The sheet is cut in a size of 1 cm² to give a sheet-shaped adhesive preparation for the oral cavity as shown in FIG. 1, wherein nicotine is contained in an amount of 4 mg per one sheet.

EXAMPLE 7

Composition for adhesive layer:

| Ingredients | Amount |
| --- | --- |
| Hiviswako | 12 g |
| Eudragit RS | 0.4 g |
| Polyethylene glycol 400 | 6 g |
| Nifedipine | 18.4 g |
| Ethanol | 120 ml |

Composition for carrier layer:

| Ingredients | Amount |
| --- | --- |
| Ethocel (STD) | 15 g |
| Castor oil | 6 g |
| Ethanol | 140 ml |

In the same manner as described in Example 1, by using the above formulation, there are prepared the composition for adhesive layer and the composition for carrier layer, respectively, and by using these compositions, there is prepared a sheet having an adhesive layer (thickness: 200 μm) and a carrier layer (thickness: 50 μm). The sheet is cut in a size of 1 cm² to give a sheet-shaped adhesive preparation for the oral cavity as shown in FIG. 1, wherein nifedipine is contained in an amount of 10 mg per one sheet.

Example 8

Composition for adhesive layer:

| Ingredients | Amount |
| --- | --- |
| Hiviswako | 12 g |
| Eudragit E | 0.25 g |
| 1,3-Butanediol | 7 g |
| Voltaren (= diclofenac sodium) | 7.18 g |
| Ethanol | 17 ml |
| Purified water | 90 ml |

Composition for carrier layer:

| Ingredients | Amount |
| --- | --- |
| Hydroxypropyl cellulose phthalate | 17 g |
| Glycerin | 3 g |
| Ethanol | 70 ml |
| Acetone | 70 ml |

In the same manner as described in Example 1, by using the above formulation, there are prepared the composition for adhesive layer and the composition for carrier layer, respectively, and by using these compositions, there is prepared a sheet having an adhesive layer (thickness: 150 μm) and a carrier layer (thickness: 100 μm). The sheet is cut in a size of 1 cm² to give a sheet-shaped adhesive preparation for the oral cavity as shown in FIG. 1, wherein Voltaren is contained in an amount of 4 mg per one sheet.

EXAMPLE 9

Composition for adhesive layer:

| Ingredients | Amount |
| --- | --- |
| Hiviswako | 12 g |
| Eudragit RS | 0.12 g |
| Polyethylene glycol 400 | 2 g |
| Titanium oxide | 0.6 g |
| Food red No. 2 pigment | 0.954 g |
| Ethanol | 140 ml |

Composition for carrier layer:

| Ingredients | Amount |
| --- | --- |
| Ethocel (STD) | 15 g |
| Castor oil | 4 g |
| Ethanol | 140 ml |

In the same manner as described in Example 1, by using the above formulation, there are prepared the composition for adhesive layer and the composition for carrier layer, respectively, and by using these compositions, there is prepared a sheet having an adhesive layer (thickness: 100 μm) and a carrier layer (thickness: 50 μm). The sheet is cut in a size of 0.5 cm² to give a sheet-shaped adhesive preparation for the oral cavity as shown in FIG. 1.

REFERENCE EXAMPLE 1

The sheet-like adhesive layer as prepared in Example 9 is cut in a size of 0.5 cm² to give a sheet-shaped adhesive preparation having no carrier layer.

The properties of the sheet-shaped adhesive preparations for the oral cavity of this invention are illustrated by the following Experiments.

EXPERIMENT 1

The preparations as prepared in Examples were used as samples as follows:

Sample A: the preparation as prepared in Example 1.
Sample B: the preparation as prepared in the same manner as described in Example 1 except that Hiviswako was omitted.
Sample C: the preparation as prepared in the same manner as described in Example 1 except that Eudragit RS was omitted.
Sample D: the preparation as prepared likewise except that Eudragit RS was used in an amount of 0.0 5 g.
Sample E: the preparation as prepared likewise except that Eudragit RS was used in an amount of 2.5 g.
Sample F: the preparation as prepared in Example 2.
Sample G: the preparation as prepared in Example 3.
Sample H: the preparation as prepared in Example 4.
Sample I: the preparation as prepared in Example 5.
Sample J: the preparation as prepared in Example 6.
Sample K: the preparation as prepared in Example 7.

Sample L: the preparation as prepared in Example 8.

These samples (each 10 sheets of round shape) were adhered on the inner side wall (at 10 points) of a one liter flash which contained 0.1 M phosphate buffer (pH 6.2, 800 ml) and was warmed at 37±0.5° C. While keeping the temperature of the liquid at 37±0.5° C., the liquid was stirred with a magnetic stirrer at 100 r.p.m. for 8 hours, and the peeling off of the test sample was observed. The results are shown in Table 1.

TABLE 1

| Sample | Number of tests | Time (hour) 0.5 | 1 | 2 | 3 | 4 | 5 | 6 | 7 | 8 | Sum of sheets peeled off | Adhesion point* |
| --- | --- | --- | --- | --- | --- | --- | --- | --- | --- | --- | --- | --- |
| A | First | 0 | 0 | 0 | 0 | 0 | 0 | 0 | 1 | 1 | 2 | 93.6 |
|   | Second | 0 | 0 | 0 | 0 | 0 | 0 | 0 | 0 | 2 | 2 | 95.6 |
|   | Average | 0 | 0 | 0 | 0 | 0 | 0 | 0 | 0.5 | 1.5 | 2 | 94.6 |
| B | First | — | — | — | — | — | — | — | — | — | — | — |
|   | Second | — | — | — | — | — | — | — | — | — | — | — |
|   | Average | — | — | — | — | — | — | — | — | — | — | — |
| C | First | 0 | 8 | 4 | 0 | 0 | 0 | 0 | 0 | 0 | 10 | 0.6 |
|   | Second | 0 | 9 | 1 | 0 | 0 | 0 | 0 | 0 | 0 | 10 | 0.3 |
|   | Average | 0 | 8.5 | 1.5 | 0 | 0 | 0 | 0 | 0 | 0 | 10 | 0.4 |
| D | First | 0 | 0 | 2 | 8 | 0 | 0 | 0 | 0 | 0 | 10 | 7.2 |
|   | Second | 0 | 0 | 1 | 7 | 2 | 0 | 0 | 0 | 0 | 10 | 9.4 |
|   | Average | 0 | 0 | 1.5 | 7.5 | 1 | 0 | 0 | 0 | 0 | 10 | 8.3 |
| E | First | 0 | 0 | 3 | 7 | 0 | 0 | 0 | 0 | 0 | 10 | 6.7 |
|   | Second | 0 | 0 | 4 | 6 | 0 | 0 | 0 | 0 | 0 | 10 | 6.1 |
|   | Average | 0 | 0 | 3.5 | 6.5 | 0 | 0 | 0 | 0 | 0 | 10 | 6.4 |
| F | First | 0 | 0 | 0 | 0 | 0 | 0 | 0 | 0 | 0 | 0 | 100 |
|   | Second | 0 | 0 | 0 | 0 | 0 | 0 | 0 | 0 | 0 | 0 | 100 |
|   | Average | 0 | 0 | 0 | 0 | 0 | 0 | 0 | 0 | 0 | 0 | 100 |
| G | First | 0 | 0 | 0 | 0 | 0 | 0 | 0 | 0 | 3 | 3 | 93.3 |
|   | Second | 0 | 0 | 0 | 0 | 0 | 0 | 0 | 0 | 2 | 2 | 95.6 |
|   | Average | 0 | 0 | 0 | 0 | 0 | 0 | 0 | 0 | 2.5 | 2.5 | 94.4 |
| H | First | 0 | 0 | 0 | 0 | 0 | 0 | 0 | 1 | 1 | 1 | 97.8 |
|   | Second | 0 | 0 | 0 | 0 | 0 | 0 | 0 | 0 | 0 | 0 | 100 |
|   | Average | 0 | 0 | 0 | 0 | 0 | 0 | 0 | 0.5 | 0.5 | 0.5 | 98.9 |
| I | First | 0 | 0 | 0 | 0 | 0 | 0 | 0 | 0 | 3 | 3 | 93.3 |
|   | Second | 0 | 0 | 0 | 0 | 0 | 0 | 0 | 0 | 3 | 3 | 93.3 |
|   | Average | 0 | 0 | 0 | 0 | 0 | 0 | 0 | 0 | 3 | 3 | 93.3 |
| J | First | 0 | 0 | 0 | 0 | 0 | 0 | 0 | 0 | 2 | 2 | 95.6 |
|   | Second | 0 | 0 | 0 | 0 | 0 | 0 | 0 | 0 | 2 | 2 | 95.6 |
|   | Average | 0 | 0 | 0 | 0 | 0 | 0 | 0 | 0 | 2 | 2 | 95.6 |
| K | First | 0 | 0 | 0 | 0 | 0 | 0 | 0 | 0 | 1 | 1 | 97.8 |
|   | Second | 0 | 0 | 0 | 0 | 0 | 0 | 0 | 0 | 1 | 1 | 97.8 |
|   | Average | 0 | 0 | 0 | 0 | 0 | 0 | 0 | 0 | 1 | 1 | 97.8 |
| L | First | 0 | 0 | 0 | 0 | 0 | 0 | 0 | 1 | 4 | 5 | 86.9 |
|   | Second | 0 | 0 | 0 | 0 | 0 | 0 | 0 | 0 | 6 | 6 | 86.7 |
|   | Average | 0 | 0 | 0 | 0 | 0 | 0 | 0 | 0.5 | 5 | 5.5 | 94.6 |

*Adhesion point is calculated by the following equation:

$$\text{Adhesion point} = \frac{\text{Sum of}\left(\begin{array}{c}\text{number of the remained} \\ \text{sheets in each time}\end{array} \times \text{time}\right)}{360} \times 100$$

(Note: time less than one hour was counted as one hour)

As is clear from the above table, Samples A, F, G, H, I, J, K and L as prepared in Examples 1 to 8 of this invention showed peeling off of only two sheets in average among 10 sheets even after 8 hours. Besides, Samples D and E which contain both carboxyvinyl polymer and methacrylic copolymer showed clear superiority to Sample C which contains no methacrylic copolymer in the time of adhesion. Sample B did not adhere onto the side wall of the flask.

EXPERIMENT 2

Sample M: the preparation as prepared in Example 9 and Sample N: the preparation as prepared in Reference Example 1 was tested as to the elution of the ingredients as follows.

Test method: According to the method for testing the elution (Paddle method) as defined in Japan Pharmacopoeia, General Test Method 44.

Figure 3:
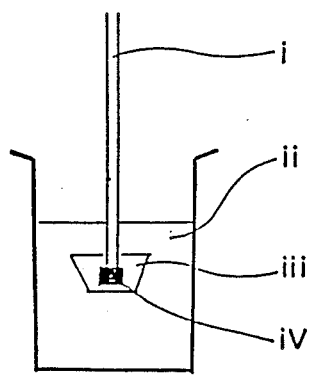
FIG. 3 shows a schematic view of a testing device used for measuring the elution of the active ingredients from the preparation.

Sample (M or N) (three sheets) were adhered onto a rotor blade, which was set in a tester for elution which contained a test solution* (250 ml) previously warmed at 37±0.5° C. so that the rotor blade was wholly dipped within the solution [see FIG. 3, wherein element i is a rotating shaft, element ii is a test solution, element iii is a rotor blade, and element iv is a sample]. The rotor blade was rotated in the solution at a fixed rate (50 r.p.m.). The eluate was collected at 15, 30, 45, 60, 90, 120, 180, and 240 minutes after the initiation of the test, and thereto was added a test solution (previously warmed at 37±0.5° C.) in the same volume as that of the eluate thus collected. There was quantitatively measured the amount of food red No. 2 pigment contained in the eluate, and the correlation between the sum of elutated amount and time was graphed as shown in the accompanying FIG. 4.

*) Test solution:

It was prepared by adding aqueous sodium hydroxide (118 ml) and water to 0.2 M potassium dihydrogen phosphate solution (250 ml) as defined in Japan Pharmacopoeia, General Test Method 36, Disintegration Test, No. 2 liquid so as to make totally 1000 ml. This solution was colorless and transparent and was pH 6.8.

Figure 4:
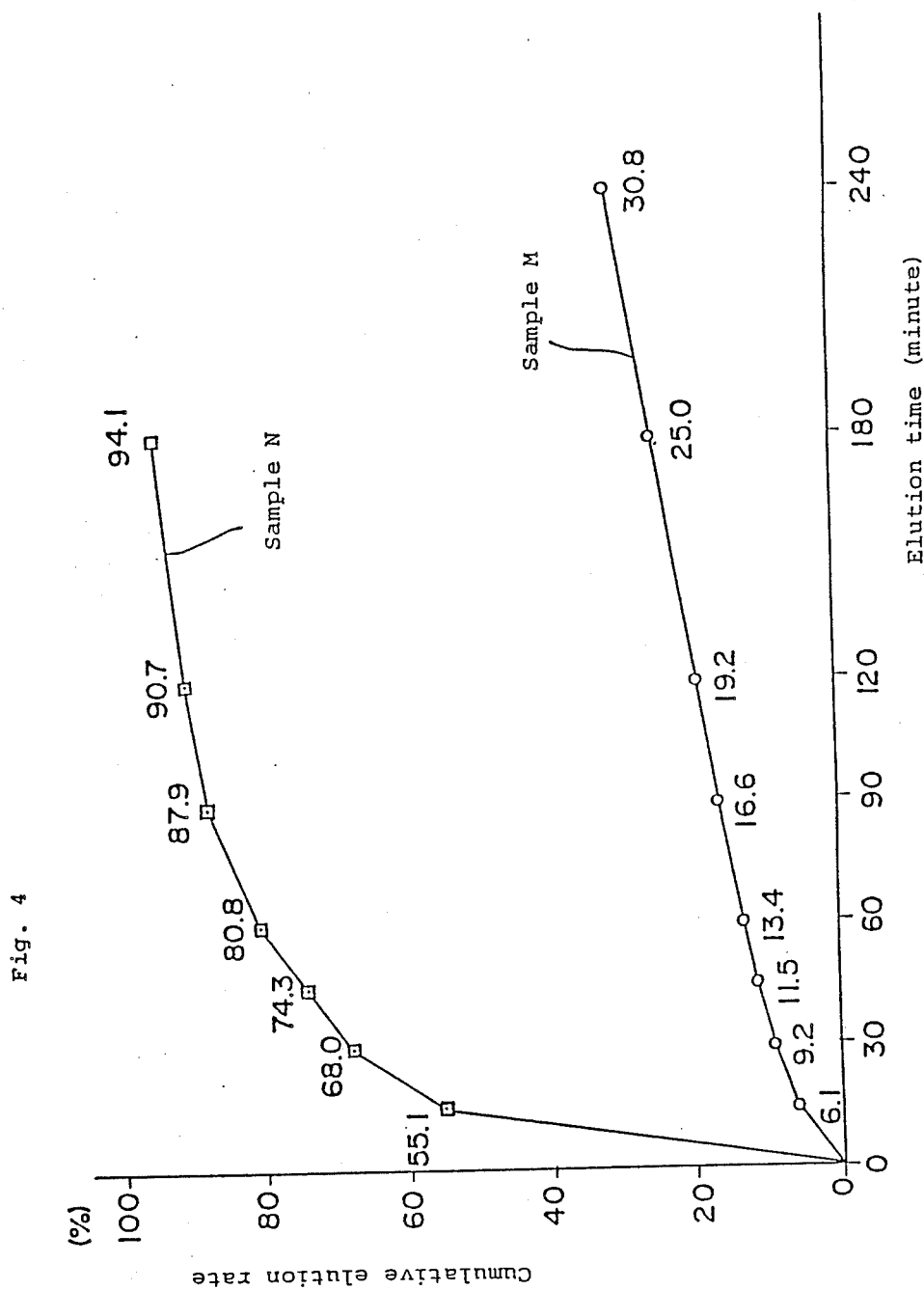
FIG. 4 is a graph showing the correlation between the sum of eluted amount of the ingredients and time which is obtained by the elution test of Sample M and Sample N.

As is shown in FIG. 4, Sample N having no carrier layer showed more than 80 % elution only one hour after the initiation of the test, but on the contrary, Sample M having a carrier layer of this invention showed only about 30 % elution even 4 hours after the initiation of the test. As is clear from the results, when the preparation of this invention is applied to the mucous membrane in the oral cavity, most of the pharmaceutically active agent contained in the preparation is released to the mucous membrane. Besides, Sample N was completely disintegrated after 3 hours, and hence, the test was stopped thereafter.

EXPERIMENT 3

There was used as a reference a commercially available adhesive preparation for the oral cavity (Sample X) having the following formulation.

Composition for adhesive layer:

| Ingredients | Amount |
| --- | --- |
| Carbopol 934 (polyacrylic copolymer) | 50 parts by weight |
| Hydroxypropyl cellulose | 50 parts by weight |
| Magnesium stearate | 0.5 parts by weight |
| Triamcinolone acetonide | 0.125 parts by weight |

Composition for carrier layer:

| Ingredients | Amount |
| --- | --- |
| Lactose | 81 parts by weight |
| Hydroxypropyl cellulose | 9 parts by weight |
| Calcium | 10 parts by weight |
| Magnesium stearate | 0.5 parts by weight |

The above Sample X and Sample A as prepared in Example 1 of this invention were subjected to the following comparative test.

3-1: Test for the elution

It was carried out in the same manner as described in Japan Pharmacopoeia, General Test Method 44, Elution test.

Rotating basket method:
Velocity: 100 r.p.m.
Test solution: The test solution* as disclosed in Example 2.

Figure 5:
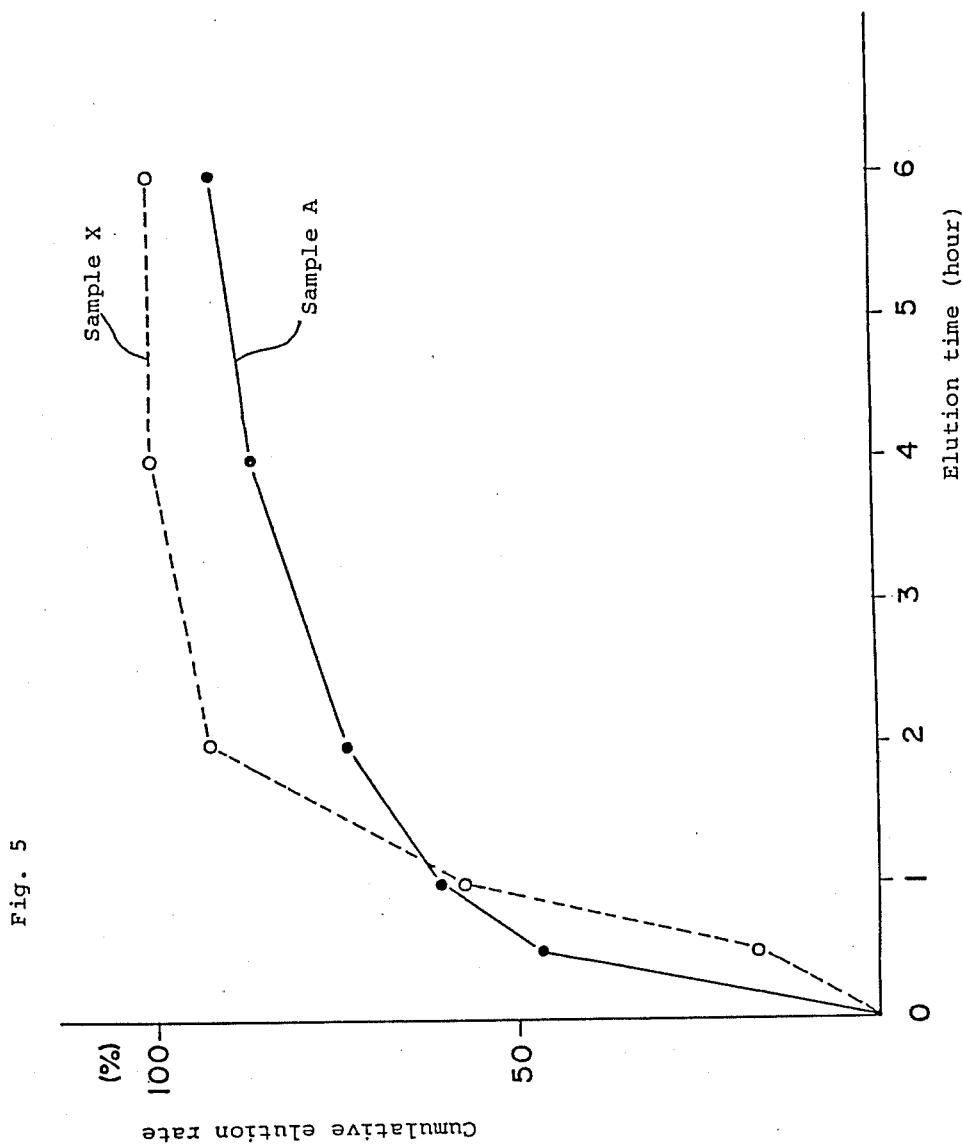
FIG. 5 is a graph showing the correlation between the sum of eluted amount of the ingredients and time which is obtained by the eltution test of Sample A and Sample X.

At each time of 30 minutes, one hour, 2 hours, 4 hours, and 6 hours after initiation of test, the whole of the eluate was exchanged, and the amount of triamcinolone acetonide contained in the eluate was quantitatively measured. The results are shown in Table 2 and FIG. 5.

3-2: Migration into 5% polyacrylamide gel

Figure 6:
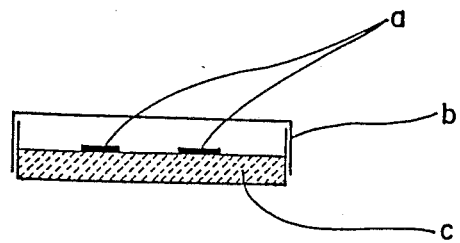
FIG. 6 shows a schematic view of an apparatus used for the migration test.

There were used six apparatuses as shown in FIG. 6 wherein a: a sample, b: a plate, c: 5% polyacrylamide gel, which were warmed at a fixed temperature (37° C.). On the 5% polyacrylamide gel contained in each plate, Sample A and Sample X (each three sheets) were each placed. After 0.5, 1, 2, 4, and 6 hours, the samples in the plate were removed, and the remaining amount of triamcinolone acetonide in the test samples was quantitatively measured, and the migration of the active agent into the polyacrylamide gel was calculated. The results are shown in Table 3 and FIG. 7.

3—3: Releasing test

Figure 8:
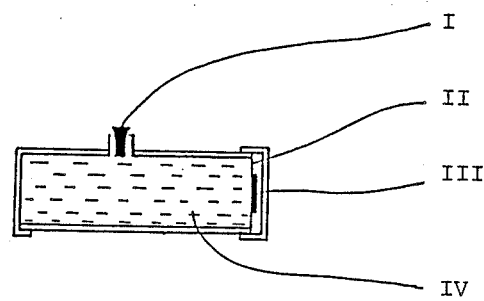
FIG. 8 shows a schematic view of an apparatus used for the releasing test.
Figure 9:
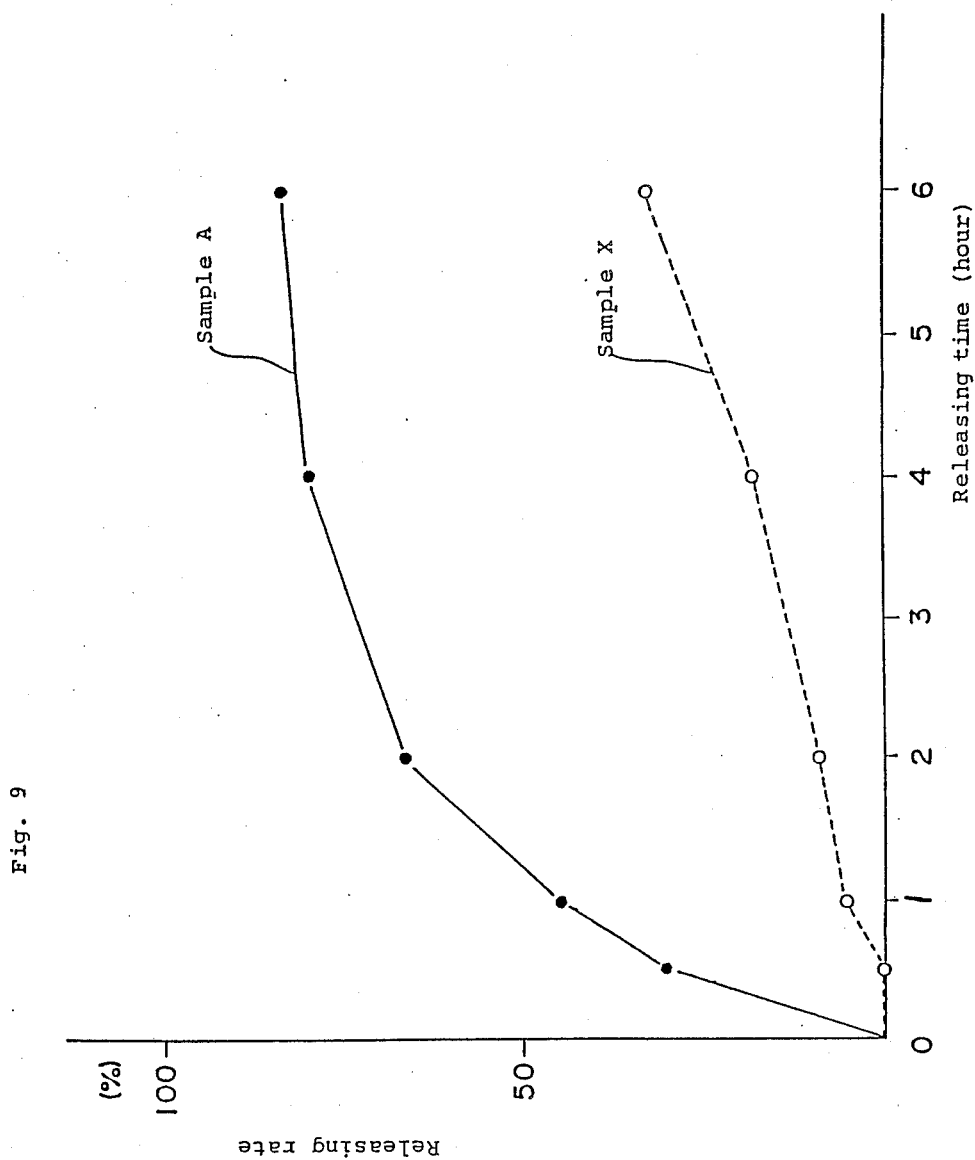
FIG. 9 is a graph showing the correlation between the releasing rate and time which is obtained by the releasing test of Sample A and Sample X.

By using an apparatus as shown in FIG. 8 wherein I: a rubber stopper, II: a dialysis membrane, III: a sample, IV: a test solution, Sample A and Sample X were each adhered onto the dialysis membrane, and the apparatus was shaken at 37° C. at a velocity of 100 strokes/min. The released solution was collected at 0.5, 1, 2, and 4 hours after the initiation of test, and thereto was added a test solution in the same volume as that of the released solution. The amount of triamcinolone acetonide contained in the released solution was quantitatively measured. The results are shown in Table 4 and FIG. 9.

TABLE 2

Test of elution (n = 3) Elution (%)

| Sample | Number of tests | Elution time (hour) | | | | |
| --- | --- | --- | --- | --- | --- | --- |
| | | 0.5 | 1 | 2 | 4 | 6 |
| A | I | 48.4 | 15.5 | 13.6 | 11.6 | 3.4 |
| | II | 47.6 | 13.7 | 13.2 | 13.8 | 5.8 |
| | III | 44.1 | 11.5 | 12.5 | 12.4 | 5.8 |
| | Average | 46.7 | 13.6 | 13.1 | 12.6 | 5.0 |
| X | I' | 20.5 | 42.1 | 30.3 | 7.1 | 0 |
| | II' | 14.1 | 42.4 | 35.0 | 8.5 | 0 |
| | III' | 16.2 | 37.6 | 39.5 | 6.7 | 0 |
| | Average | 16.9 | 37.6 | 39.5 | 6.7 | 0 |

TABLE 3

Migration test into 5% polyacrylamide gel (n = 3) Migration (%)

| Sample | Number of tests | Time (hour) | | | | | |
| --- | --- | --- | --- | --- | --- | --- | --- |
| | | 0.5 | 1 | 2 | 4 | 6 | 8 |
| A | I | 16.9 | 17.7 | 36.5 | 33.9 | 46.3 | 49.8 |
| | II | 18.4 | 26.9 | 30.5 | 47.1 | 44.8 | 53.7 |
| | III | 16.6 | 26.5 | 33.9 | 39.5 | 44.8 | 54.9 |
| | Average | 17.3 | 23.7 | 33.6 | 40.2 | 45.3 | 52.8 |
| X | I' | 0 | 7.9 | 9.6 | 15.3 | 20.5 | 18.6 |
| | II' | 2.8 | 1.0 | 16.3 | 17.2 | 22.2 | 23.2 |
| | III' | 7.7 | 7.3 | 13.1 | 16.0 | 19.9 | 21.4 |
| | Average | 3.5 | 5.4 | 13.0 | 16.2 | 20.9 | 21.1 |

TABLE 4

Releasing test (%)

| Sample | Number of tests | Releasing time (hour) | | | | |
| --- | --- | --- | --- | --- | --- | --- |
| | | 0.5 | 1 | 2 | 4 | 6 |
| A | I | 30.9 | 43.8 | 67.2 | 85.5 | 84.8 |
| | II | 31.9 | 47.3 | 70.3 | 78.4 | 87.2 |
| | III | 27.0 | 42.8 | 61.9 | 76.3 | 78.4 |
| | Average | 29.9 | 44.6 | 66.5 | 80.1 | 83.5 |
| X | I' | 0 | 4.7 | 8.5 | 16.9 | 30.1 |
| | II' | 0 | 3.7 | 8.1 | 19.5 | 35.0 |
| | III' | 0 | 6.8 | 10.7 | 18.2 | 32.5 |
| | Average | 0 | 5.1 | 9.1 | 18.2 | 32.5 |

As is clear from the above results, although Sample X was 100% eluted after 4 hours in the elution test, it showed only about 10% migration and release after 4 hours. It is assumed from the results that most of the pharmaceutically active agent contained in Sample X would not have been released at the surface of the mucous membrane, but would have been swallowed.

On the other hand, Sample A of this invention showed high migration and release in the migration test and releasing test and showed simultaneously prolonged migration of the agent. From the results, it is clear that the preparation of this invention is advantageous as an adhesive preparation for the oral cavity.

EXPERIMENT 4

The preparations of this invention (Sample A as prepared in Example 1 and Sample F as prepared in Example 2) and the reference preparation (Sample X) were adhered onto the mucous membrane (on the interior surface of the mouth at the cheek surface facing the teeth) of 20 healthy volunteers, and their opinions were obtained on the questionaires such as the time of adhering, the degree of strange sensation, ease of application, and ease of peeling off. The results are shown in Tables 5 and 6.

Time and manner of adhering: At 9 a.m. the samples were adhered onto the mucous membrane in the oral cavity, and the test was continued until 5 p.m. (for 8 hours), but when the sample was peeled off or lost before 8 hours, the test was terminated. When the sample was still adhering at 5 p.m., the sample was peeled off by hand, and thereby the ease of peeling off was tested. During the test, the volunteers took a soft drink twice and meal once. In Table 5, the number of persons means the number whose sample was peeled off or lost.

TABLE 5

Adhering time (Number of persons)

| Sample | Less than 1 | 2 | 3 | 4 | 5 | 6 | 7 | 8 |
|---|---|---|---|---|---|---|---|---|
| A | 0 | 0 | 0 | 1 | 7 | 9 | 1 | 1 |
| F | 0 | 0 | 0 | 0 | 0 | 0 | 1 | 3 |
| X | 6 | 9 | 1 | 0 | 0 | 0 | 0 | 0 |

TABLE 6

Strange sensation, ease of application and peeling off (Number of persons)

| Items | | Sample A | Sample F | Sample X |
|---|---|---|---|---|
| Strange sensation | Always felt | 5 | 1 | 18 |
| | Occasionally felt | 11 | 3 | 2 |
| | Not felt | 4 | 16 | 0 |
| Ease of application | Easily applied | 14 | 14 | 4 |
| | Hardly applied | 3 | 2 | 10 |
| | Indistinct | 3 | 4 | 6 |
| Ease of peeling off | Easily peeled off | 1 | 7 | — |
| | Peeled off with difficulty | — | 8 | — |
| | Indistinct | — | 1 | — |

EXPERIMENT 5

The pharmacological effect of the preparation of this invention was tested by the inhibitory effect thereof on the hyperpermeability of blood vessel wall induced by irritation with xylene at the mucous membrane in the oral cavity in the hamster.

Samples to be tested:
There were used the sheet-shaped adhesive preparation for the oral cavity containing triamcinolone acetonide as prepared in Example 1 (Sample A) and a reference preparation containing the same amount of triamcinolone acetonide (Sample X). Test method:

Hamster was used as a test animal. To the animal was intravenously administered 1% Evan's blue (0.5 ml/100 g body weight) under light anesthesia, and immediately the right cheek was exposed and irritated with a felt (diameter: 10 mm) impregnated with xylene for 30 seconds, and thereafter, the test sample was adhered to the same site. It was adhered for 0.5, 1, 2 or 4 hours. After lapse of the fixed time, the right cheek was cut out together with skin, and the site adhered with the test sample was punched out in a size of a diameter of 7 mm, and the mucous membrane was peeled off. The mucous membrane was dipped in a mixture of acetone - 0.3 % $Na_2SO_4$ (7:3) for 16 to 20 hours, and the eluted pigment was extracted and the absorbence thereof was measured with a spectrophotometer at a wavelength of 620 nm. The results are shown in Table 7, wherein the absorbance was shown as a mean absolute value.

TABLE 7

Ihibitory effect against the hyperpermeability of blood vessel wall at the mucous membrane in cheek of hamster (n = 10)

| Sample | Treating time (hour) | | | |
|---|---|---|---|---|
| | 0.5 | 1.0 | 2.0 | 4.0 |
| Control (not treated) | 39.4 | 42.8 | 44.8 | 45.8 |
| Sample A | 14.2 | 9.5 | 8.9 | 13.7 |
| Sample X | 16.6 | 13.6 | 11.7 | 16.9 |

As is clear from the above results, Sample A of this invention showed an inhibition of 64 to 80% at 0.5 to 4 hours which was more than 10% higher than the data for refrence Sample X, which means that the preparation of this invention is superior as an adhesive preparation applicable to the oral cavity.

What is claimed is:

1. A sheet-shaped adhesive pharmaceutical preparation capable of adhering within the oral cavity which comprises an adhesive layer containing as essential components a carboxyvinyl polymer, a water-soluble methacrylic copolymer, a polyhydric alcohol and a pharmaceutically active agent, and a water-impermeable and water-insoluble carrier layer containing as essential components a pharmaceutically acceptable water-insoluble, film-forming high molecular weight compound and a plasticizer, wherein the ingredients of the adhesive layer are substantially released from one side of the sheet-shaped preparation whereby the ingredients are absorbed through the mucous membrane, or teethridge to which it is adhered.

2. The sheet-shaped adhesive preparation according to claim 1, wherein the water-insoluble, film-forming high molecular weight compound is a water-insoluble cellulose derivative.

3. The sheet-shaped adhesive preparation according to claim 1, wherein the carboxyvinyl polymer and the waterinsoluble methacrylic copolymer are incorporated in a ratio of 5:1 to 200:1 by weight.

4. The sheet-shaped adhesive preparation according to claim 1, wherein the adhesive layer has a thickness of 10 to 480 μm and the carrier layer has a thickness of 10 to 200 μm, and the total thickness of the preparation is in the range of 20 to 500 μm.

5. The adhesive pharmaceutical preparation of claim 1 wherein the water-insoluble methacrylic copolymer used for the adhesive layer is selected from the group consisting of ethyl acrylate-methyl methacrylate-trimethyl-ammonium-ethyl methacrylate chloride polymer, dimethylaminoethyl methacrylate, methyl methacrylate copolymer and mixtures thereof.

6. The adhesive pharmaceutical preparation of claim 1 wherein the carboxyvinyl polymer is polyacrylic acid or a partially crosslinked product thereof.

7. The adhesive pharmaceutical preparation of claim 1 wherein the polyhydric alcohol is a member selected from the group consisting of glycerin, propylene glycol, polyethylene glycol, 1,3-butane-diol, sorbitol and mixtures thereof.

8. The adhesive pharmaceutical preparation of claim 1 wherein the water-insoluble, film-forming high molecular weight compound used for the carrier layer is a member selected from the group consisting of a water-insoluble cellulose derivative having 1.5 or more of degree of substitution of the ethoxy group, cellulose acetate phthalate, hydroxypropyl methyl cellulose pathalate, and mixtures thereof.

9. The adhesive pharmaceutical preparation of claim 8 wherein the water-insoluble cellulose derivative is ethyl cellulose.

10. The adhesive pharmaceutical preparation of claim 1 wherein the plasticizer is a member selected from the group consisting of castor oil, triacetin, glycerin, propylene glycol, polyethylene glycol, 1,3-butane-diol, sorbitol and mixtures thereof.

11. The adhesive pharmaceutical preparation of claim 1 wherein the pharmaceutically active agent is a medicament which can be absorbed from the mucous membrane in the oral cavity.

12. The adhesive pharmaceutical preparation of claim 11 wherein the medicament is selected from the group consisting of benzodiazepin analogs, psychotropic agents, antispasmodics, antihistamines, steroidal and non-steroidal antiinflammatory agents, cardiotonics, antiarrhythmic agents, diuretics, antihypertensives, vasoconstrictors, vasodilators, nitrate agents, calcium antagonists, antiallergic agents, agents for oral diseases, agents for dental diseases, hormones, vitamins, agents for quitting smoking, antitumor agents, antibiotics, and chemotherapeutics.

13. The adhesive pharmaceutical preparation of claim 3 wherein the weight of both the carboxyvinyl polymer and the methacrylic copolymer is in the range of 60 to 95 w/w% based on the total weight of all components in the adhesive layer.

14. The adhesive pharmaceutical preparation of claim 1 wherein the polyhydric alcohol is present in an amount of 5 to 20 w/w% based on the total weight of all components in the adhesive layer.

15. The adhesive pharmaceutical preparation of claim 1 wherein the pharmaceutically active agent is present in an amount of 1 to 30 w/w% based on the total weight of the adhesive layer.

16. The adhesive pharmaceutical preparation of claim 1 wherein the water-insoluble, film-forming high molecular weight compound and the plasticizer in the water-inpermeable and water-insoluble carrier layer are incorporated in a weight ratio of 10:1 to 3:2.

* * * * *